(12) United States Patent  
Burress

(10) Patent No.: US 11,371,005 B2  
(45) Date of Patent: Jun. 28, 2022

(54) MONITORING CHAMBER

(71) Applicant: Edward Francais Burress, Washougal, WA (US)

(72) Inventor: Edward Francais Burress, Washougal, WA (US)

( * ) Notice: Subject to any disclaimer, the term of this patent is extended or adjusted under 35 U.S.C. 154(b) by 267 days.

(21) Appl. No.: 16/883,781

(22) Filed: May 26, 2020

(65) Prior Publication Data

US 2021/0371798 A1 Dec. 2, 2021

(51) Int. Cl.
*C12M 1/42* (2006.01)
*C12M 1/00* (2006.01)
*B01L 3/00* (2006.01)
*C12M 1/34* (2006.01)

(52) U.S. Cl.
CPC ....... *C12M 35/04* (2013.01); *B01L 3/502715* (2013.01); *C12M 23/58* (2013.01); *B01L 2300/0627* (2013.01); *C12M 41/12* (2013.01); *C12M 41/34* (2013.01); *C12M 41/40* (2013.01)

(58) Field of Classification Search
CPC ...... B01L 3/502715; B01L 3/00; B01L 13/00; B01L 7/52; B01L 7/00; B01L 2200/147; B01L 2200/146; B01L 2300/0627; B01L 2300/0829; C12M 35/04; C12M 23/58; C12M 23/48; C12M 41/12; C12M 41/34; C12M 41/40; C12M 41/48; C12M 41/36; C12M 41/26; C12M 41/0014; C12M 33/00
See application file for complete search history.

(56) References Cited

U.S. PATENT DOCUMENTS 9,556,413 B2 * 1/2017 Venter .................... C12M 23/44  
2019/0310179 A1 * 10/2019 Sekimoto ............... G01N 15/06

* cited by examiner

*Primary Examiner* — Michael L Hobbs  
(74) *Attorney, Agent, or Firm* — Mark S Hubert

(57) ABSTRACT

A bypass flow monitoring chamber that may be retrofit onto the main chamber of an incubation chamber, for continuous collection of environmental samples. This allows for the measurement and correction of the environmental conditions within the chamber, and the return of the sample to the main chamber. Utilizing this sampling method, the separable bypass flow monitoring chamber may be isolated from the main chamber by a set of valves during a period of high-heat decontamination of the incubator therein protecting the sensors and contents of this separable chamber, as well as allowing the use of less expensive and lower temperature rated incubator sensors.

10 Claims, 2 Drawing Sheets

MONITORING CHAMBER

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to a system to prolong the life of sensors, and to allow cheaper sensors to be used in culture incubators, and more particularly to incubator decontamination design technology.

BACKGROUND

Incubators for cell culture growth utilize a variety of heating and environmental parameter control sensors to control not only temperature, but gas concentrations (such as oxygen, nitrogen, and carbon dioxide) and relative humidity. Since an incubator for cell culture will typically operate in the 37 to 55 degree centigrade range, it is important to keep the cell cultures hydrated, and preventing them from drying out. Along with the growth of the desired cell cultures, the environment within the cell also promotes the growth of unwanted organisms within the cell. For this reason, a primary consideration when designing or operating an incubator is its ability to be decontaminated.

Chemicals and cleaning agents such as Quaternary ammonium compounds; Hydrogen Peroxide; acetic acid peroxide; Ethanol; Isopropanol; formaldehyde and chlorine bleach are commonly used on economy model incubators which lack automatic cleaning ability. While these save cost in the incubator, they rely on physical labor to scrub all internal surfaces with the cleaning agent, and require specialized safety equipment to prevent exposure to the laboratory technician. Decontamination relies solely on the effectiveness of the cleaning agents and the thoroughness of the operator.

Other decontamination methods exist using ultraviolet light to deactivate the ability of micro-organisms from reproducing. While ultraviolet decontamination can be automated, unfortunately it is less effective since the UV rays cannot effectively decontaminate behind a physical object with reflected light. Only the micro-organisms in an unobstructed exposure from a sufficient watt density ultraviolet source between 280 nm and 315 nm will be effectively decontaminated.

Another method of incubator decontamination is that of high temperature. Exposure to 180 degrees centigrade for two hours will decontaminate an incubator from most micro-organisms including spores. Incubators exist on the market which perform this task well.

Generally, high temperature decontamination requires that any sensors in the chamber be removed along with cell culture trays, shelving or other apparatus which can be damaged by exposure to high temperatures. Failure to remove the sensors can result in failure of the incubator to enter high heat decontamination mode, or failure of the sensors.

While sensors have been developed using special technology and materials to operate at elevated temperatures, they are expensive by a factor of ten-fold over conventional sensors. Additionally, these high temperature sensors still can only endure a finite number of high-heat decontamination cycles before they need replacement. Finally, these high temperature sensors require special electrical connections which can withstand not only the high heat exposure, but the warm humid environment within the incubator and the caustic environment caused by carbonic acid, which is a byproduct of CO2 incubators.

Henceforth, a method and apparatus which can allow lower cost, higher reliability sensors to be used to monitor incubation chamber environmental conditions without being exposed to the high temperatures of the decontamination cycles would fulfill a long felt need in the industry. This new invention utilizes and combines known and new technologies in a unique and novel configuration to overcome the aforementioned problems and accomplish this.

BRIEF SUMMARY

In accordance with various embodiments, a method and apparatus to allow the high temperature decontamination of a cell culture incubation chamber that will not damage the environmental sensors, and allow for the use of more efficient, cheaper, non-high temperature rated sensors. This apparatus is a sensor sparing monitoring chamber that may be retrofit onto an incubation chamber. The method of decontamination this affords does not require removal of the sensors. Lastly, the monitoring system that this retrofit incubation chamber monitoring chamber houses, has a reliable service life beyond that of current high-temperature sensor solutions Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION OF CERTAIN EMBODIMENTS

Figure 1:
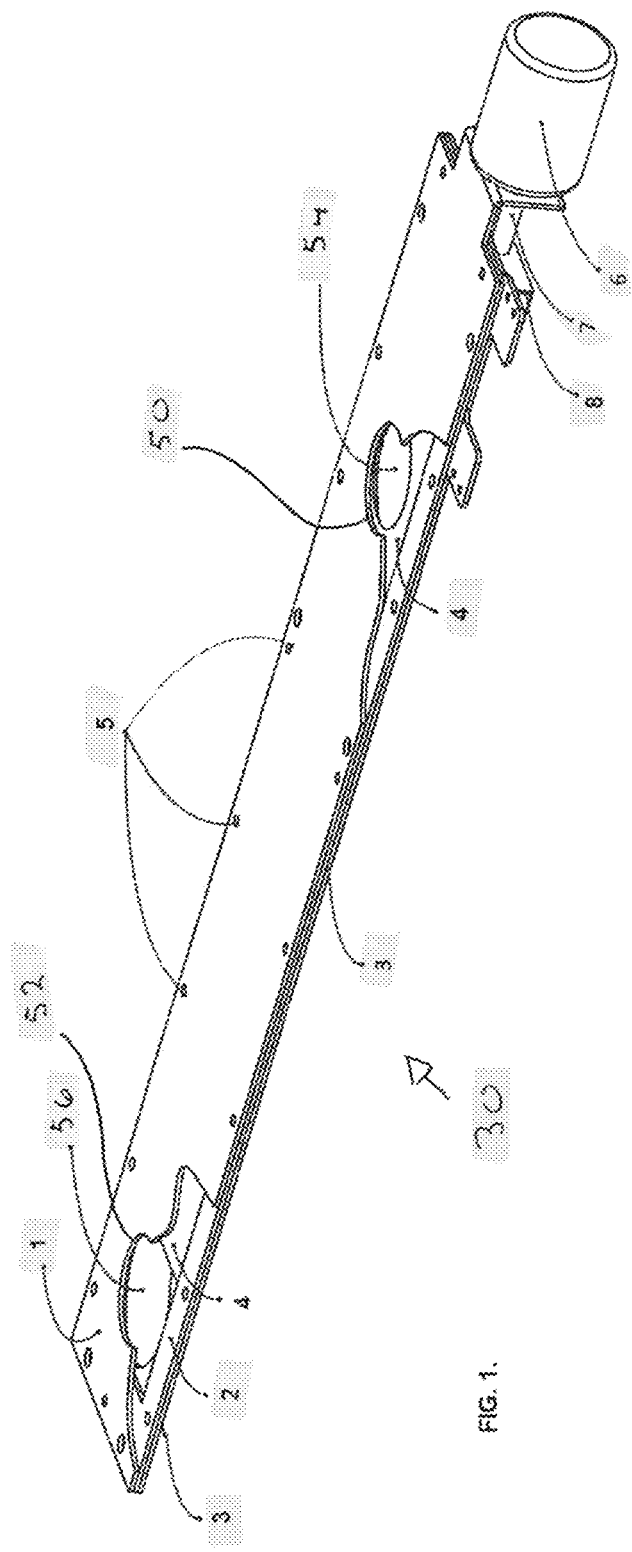
FIG. 1 is a top view of the retrofit monitoring chamber.
Figure 2:
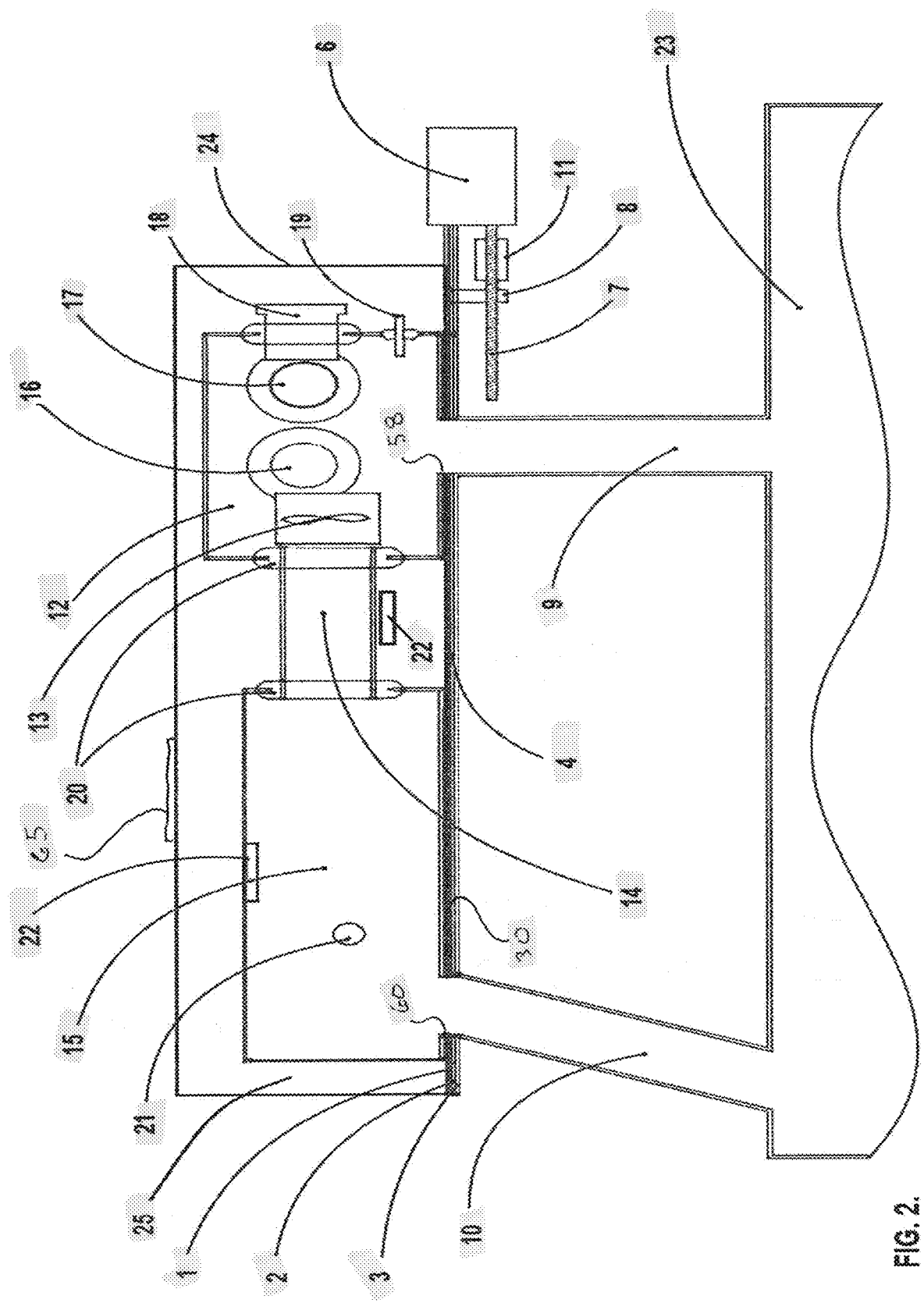
FIG. 2 is a perspective view of the slide gate assembly.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the following description, for the purposes of explanation, numerous specific details are set forth in order to provide a thorough understanding of the described embodiments. It will be apparent to one skilled in the art, however, that other embodiments of the present invention may be practiced without some of these specific details. It should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

As used herein, the term "retrofit" refers to a component or accessory that can be added to something that did not have the component or accessory on it when manufactured.

As used herein, the term "gate valve" refers to a valve that opens by sliding a barrier out of the path of the fluid or gas. They are also known as a sluice valve and in various configuration called blast gates, knife gates, and the like. Gate valves have a shallow profile and require very little space along the linear axis of the pipe or conduit so as to minimally restrict the flow the gate is fully opened. The gate faces can be parallel or wedge-shaped.

As used herein, the term "environmental sensors" refers to electronic devices that generate and transmit signals proportional to level of a specific environmental characteristic of the environment they are placed in. These include, but are not limited to, temperature sensors, humidity sensors, pH sensors, specific chemical sensors including but not limited to CO, $CO^2$, $O^2$ sensors, air pressure sensors, air flow sensors, particulate sensors, specific gas sensors, VOC sensors, and the like. Their transmitted signals are interpreted and output in a readable format by a processing device.

The present invention relates to a novel design for a sensor sparing, temperature controlled monitoring chamber that may be retrofit onto an existing incubation chamber. The overarching principal is to provide a heated gas rail housing with a gas rail therein that can be retrofit onto an existing incubation chamber. The gas rail is an enclosed fluid path made of a sensor chamber and a correction chamber connected by a quartz tube that can be isolated from the main incubation chamber by gate valves so as to prevent the hot, corrosive, humid gas generated during high temperature decontamination from damaging the sensitive environmental monitoring sensors housed in the sensor chamber. This retrofit chamber allows for the extended use of economically priced environmental sensors rather than high temperature rated sensors and their associated mechanical and electrical connectors. It offers consumers the ability to upgrade their incubation chambers without replacing them. The gas rail allows for the sampling and subsequent adjustment/correction of the environmental conditions in the incubation chamber.

Placing the sensors in a separate thermally controlled chamber in selectable communication with the main incubation chamber allows air from the main chamber of the incubator, to be drawn by a fan into the gas rail, be sampled, passed through a quartz tube with adjacent UV decontaminating lights, and have its chemical composition corrected, if necessary, and returned. This gas rail can be isolated from the incubation chamber via a baffle, blast gate, iris, or similar closure so that during the period that the main chamber temperature is increased above 50 degrees Centigrade for decontamination, the gas rail and sensors will no longer be in communication with the main chamber, but rather will remain in a low temperature environment in the gas rail, thereby protecting the sensors.

Looking at FIG. 1, it can be seen that the monitoring chamber 24 is a rigid, sealed enclosure, generally cuboid in configuration with an inlet open-ended inlet passage 9 and an open-ended outlet passage 10 extending from its exterior wall. These two passages in the preferred embodiment are stainless steel tubes or channels that connect the monitoring chamber 24 to the incubation chamber 23. In the preferred embodiment these tubes are welded around 12-75 mm orifices, 0.25 to 1.5 m separated, that are cut through the wall of the incubation chamber and the wall of the monitoring chamber 24, although in alternate embodiments the ends of these passages may be affixed with a plethora of well-known gas tight fittings, including but not limited to threaded nipples, compression fittings or the equivalent. These passages extend outward beyond any insulation and heat source which is used to keep the main chamber of the incubation chamber at the proper temperature.

The monitoring chamber 24 is a heated environment having a heat source 65 that provides a heated air jacket 25 around the entire gas rail.

Fastened to the wall of the monitoring chamber 24 is a dual blast gate valve 30. The dual blast gate valve 30 is made of a top cover 1, a bottom cover 3, a middle guide 2 and a slider plate 4. The dual blast gate valve 30 is a planar arrangement with the slider plate 4 slidingly fit within the middle guide 2 and this arrangement sandwiched and firmly clamped together by the top and bottom covers 1 and 3 with perimeter mechanical fasteners 5, to form a sealed valve assembly. There is an inlet port 50 and an outlet port 52 that is formed between the top cover 1 and bottom cover 3 by aligned circular orifices cut therethrough each of these covers. The top cover has the first inlet orifice and the first outlet orifice formed therethrough while the bottom cover 3 has the second inlet orifice and the second outlet orifice cut therethrough. (The middle guide 2 has no material in these regions as it surrounds and guides the perimeter of the slider plate 4.) The inlet port 50 corresponds to the alignment of the first inlet orifice and the second inlet orifice. The outlet port 52 corresponds to the alignment of the first outlet orifice and the second outlet orifice. The slider plate 4 is constrained within the assembly and is free to move to simultaneously open and close the inlet port 50 and the outlet port 52. The regions of the slider plate 4 that seal or block the inlet port 50 and outlet port 52 are called the inlet gate 54 and the outlet gate 56. The only other opening in the dual blast gate valve 4 is an orifice to allow the slider plate 4 to attach to its mechanized linkage.

This valve 30 may be manipulated either manually or through action of a servo motor to traverse the slider plate 4 within and along the linear axis of the valve 30 to simultaneously position its inlet gate 54 and outlet gate 56 across the inlet port 50 and outlet port 52 to open or close the open-ended inlet passage 9 and an open-ended outlet passage 10.

In the preferred embodiment, the valve 30 is operated in a mechanized fashion utilizing an electric gear motor 6 to spin it attached threaded rod 7 is that is in communication with the slider plate 4 by a flexible coupler 11 and a threaded nut assembly 8 attached to the slider plate 4. By commanding the motor 6 to turn clockwise or counterclockwise, the slider plate 4 may slide within the valve 30 to open or close the inlet port 50 and outlet port 52.

Attached to the inlet port 50 and outlet port 52 on the top cover 1 of the dual blast gate valve 30 are an inlet stub channel 58 and an outlet stub channel 60 which form pathways between the inlet gate 54, the outlet gate 56 thus continuing the open-ended inlet passage 9 and an open-ended outlet passage 10 from the incubation chamber 23 to the gas rail. This gas rail is a long, narrow, sealed, gas tight tunnel within the monitoring chamber 24 which in the preferred embodiment is approximately 75 mm by 75 mm by up to 1.5 meters long. The entire gas rail is thermally controlled at a slightly elevated temperature with respect to that of the main monitoring chamber 24 to prevent condensation which occurs when warm moist air comes in contact with a cooler surface or area. The gas rail is surrounded by the air jacket 25 which is the temperature controlled atmosphere in the monitoring chamber 24 volume.

The gas rail is made up of a sensor chamber 12 having a sensor chamber inlet and a sensor chamber outlet, a balancing chamber 15 having a balancing chamber inlet and a balancing chamber outlet, and a quartz tube 14 connected in a gas tight fashion between the sensor chamber outlet and the balancing chamber inlet utilizing a pair of gas tight seals 20 preferably two high-temperature silicone grommets. A fan 13 contained in the gas rail draws the incubator gasses from the incubation chamber 23 into the gas rail and then pushes these gasses back into the incubation chamber, adjusted or not.

The sensor chamber 12 contains an area for environmental sensors for measuring oxygen, carbon dioxide, temperature, and humidity at a minimum. Preferably it will contain a $CO^2$ sensor 16, and $O^2$ sensor 17, a pressure transducer 18 and a combination relative humidity and temperature sensor 19. Optionally, it may include a sensor for measuring atmospheric pressure.

Preferably, the fan 13 is located within the sensor chamber 12 and is an IP-68 rated fan that is positioned such that it draws air in and across the various sensors, exiting at the far end of the gas rail where it is returned to the incubation chamber 23. The data outputs of the various sensors are sent to a central processing means (wired or wirelessly) which monitors the environmental conditions in order to report and correct the conditions. The processing means (not illustrated) provides readings interpreted from the data which allows the operator or a mechanized system to make the corrections in the balancing chamber 15.

The balancing chamber 15 contains valve-controlled injection ports 21 for inserting any necessary gasses such as oxygen, nitrogen, or carbon dioxide to adjust and correct the gas concentrations in the incubation chamber 23. If concentrations of any gas are too low, the appropriate gas will be added by action of the central controller and the appropriate gas admission valve into the injection ports 21. Conversely, if any concentration of a given gas becomes too high as reported by the sensors, the central controller will cause other valves to inject other gasses in the appropriate amount to bring the gas concentration back into balance.

There are UV light sources 22 in the balancing chamber 15 and outside of the quartz tube 14. These operate in the UV-C range which can be activated to decontaminate any potential micro-organisms.

An additional area for generating humidity may also be included as an option which can open and close by a similar but separate blast gate. This optional humidity generation area may communicate with the gas rail in the balancing chamber and be located downstream of the sensors and fan such that it cannot create a false reading on the relative humidity measured.

In operation, the method of sampling, correction and sensor protection proceeds as follows. During normal operation an incubator 23, (also called a cell culture main chamber) contains samples desired to be under stable environmental control including temperature, gas concentration, and humidity. Two connecting tubes to the monitoring chamber 24, an inlet passage 9 and an outlet passage 10, are open to allow free flow of air between the incubation chamber 23 and the gas rail of the monitoring chamber 24.

During the operation of the gas rail, incubation chamber air is drawn upward through the inlet passage 9 by action of the fan 13. The air enters the sensor chamber 12 where it may be sampled by a $CO^2$ sensor 16, and $O^2$ sensor 17 a pressure transducer 18 and a combination relative humidity and temperature sensor 19. Samples may be taken continuously, or periodically as required. After being sampled for all environmental conditions, the air exits the sensor chamber 12 through the fan 13 into a clear quartz tube 14 which connects the sensor chamber 12 to the balancing chamber 15. The quartz tube 14 being sealed gas-tight seal at each end with high-temperature silicone grommets 20. As the air passes through the quartz tube 14, any micro-organisms which may be entrained in the air stream are exposed to ultraviolet light in the UV-C range by a UV-C light source 22. UV-C light being the most effective wavelength at deactivating the reproductive cycle of organic life, passes through the quartz tube 14 being transparent to UV-C wavelengths. The air then exits the quartz tube 14 and enters the balancing chamber 15. Within the balancing chamber 15 is a second UV-C light source 22 which is responsible for deactivating any resident micro-organisms within the balancing chamber 15. A gas inlet 21 from a manifold containing a plurality of electrically activated valves allows specific gas concentrations to enter the balancing chamber 15 to correct any out of balance gasses which may have been reported by sensors in the sensor chamber 12. Once the proper amount of correcting gasses have been injected into the correction chamber 15, airflow created by the fan 13 urges the corrected gas concentrations back into the incubation chamber 23. In order to prevent condensation from forming within any element of the gas rail, the entire assembly of sensor chamber and sensors, quartz tube, balancing chamber and all associated attaching components are contained within a heated monitoring chamber 24 forming a heated space known as an air jacket 25.

During high heat decontamination of the incubation chamber 23, the motor 6 is operated to move the slider plate 4 via a flexible coupler 11, threaded shaft 7 and threaded nut 8 to close the inlet passage 9 and the outlet passage 10. By closing these openings, the gas rail and especially the sensors in the sensor housing are protected from the higher temperatures required to decontaminate the incubation chamber which could damage them if exposed. The sensors 16-19 in the sensor chamber 12 are rated at approximately 50 degrees Celsius, while the decontamination temperature in the main chamber will reach 180 degrees C. and be held there for a period of two hours. The heat source in the monitoring chamber 24 is turned off so that the temperature in the gas rail air jacket 25 may remain below 50 degrees Celsius during the entire decontamination cycle. UV-C light sources 22 are turned on. The fan 13 is turned off. The incubation chamber 23 is brought under control to 180 degrees Celsius and maintains that temperature for 2 hours. At the end of the two hours, the heat to the incubation chamber is turned off and allowed to cool through natural convection and conduction of the materials. When the temperature of the incubation chamber is measured to be below 50 degrees Celsius, the slider plate 4 is opened by reversing the direction of the gear motor 8 and drawing the slider plate 4 toward the motor 8 causing the two ports 50 and 52 to open. If for any reason the decontamination cycle is interrupted, the system controller will set a notice alerting the operator that the cycle did not complete successfully.

While certain features and aspects have been described with respect to exemplary embodiments, one skilled in the art will recognize that numerous modifications are possible. Moreover, while the procedures of the methods and processes for building, assembling and using the device described herein is described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. It will be appreciated that the invention is intended to cover all modifications and equivalents within the scope of the following claims.

Having thus described the invention, what is claimed as new and desired to be secured by Letters Patent is as follows:

1. A monitoring chamber adapted to be retrofit onto an incubation chamber comprising:
    a sensor chamber having a sensor chamber inlet end and a sensor chamber outlet;
    a balancing chamber having a balancing chamber inlet and a balancing chamber outlet;
    a quartz tube connected in a gas tight fashion between said sensor chamber outlet and said balancing chamber inlet;
    a monitoring chamber encasing said sensor chamber, said balancing chamber and said quartz tube;
    an open-ended inlet passage extending between said incubation chamber and said monitoring chamber placing said incubation chamber and said sensor chamber in fluid communication;
    an open-ended outlet passage extending between said incubation chamber and said monitoring chamber placing said incubation chamber and said balancing chamber in fluid communication; and
    a dual blast gate valve affixed to a side wall of said monitoring chamber, said dual blast gate valve having a slider plate with an inlet gate region positioned about said inlet passage and an outlet gate region positioned about said outlet passage;
    wherein said inlet gate region is slidingly positionable between said inlet passage and said sensor chamber, and said outlet gate region is slidingly positionable between said outlet passage and said balancing chamber;
    wherein a gas rail is formed in the volume encased by said sensor chamber said quartz tube and said balancing chamber; and
    a fan housed within said gas rail to direct the flow of gas between said inlet passage and said outlet passage.

2. The monitoring chamber of claim 1 wherein when said inlet gate region is situated between said open ended inlet passage and said sensor chamber of said gas rail, and wherein said outlet gate region is simultaneously situated between said open ended outlet passage and said balancing chamber of said gas rail.

3. The monitoring chamber of claim 1 further comprising:
    a first UV-C light source adjacent said quartz tube;
    a second UV-C light source adjacent a balancing chamber.

4. The monitoring chamber of claim 1 further comprising:
    an environmental sensor operably installed in said sensor chamber, said environmental sensor selected from the group of environmental sensors consisting of one or more of O2 sensors, CO2 sensors, CO sensors, relative humidity sensors, temperature sensors, or pressure sensors.

5. The monitoring chamber of claim 2 further comprising:
    an environmental sensor operably installed in said sensor chamber, said environmental sensor selected from the group of environmental sensors consisting of one or more of O2 sensors, CO2 sensors, CO sensors, relative humidity sensors, temperature sensors, or pressure sensors.

6. The monitoring chamber of claim 2 wherein said dual blast gate further comprises:
  a guide plate mounted on said monitoring chamber having a first inlet orifice and a first outlet orifice formed therethrough;
  a cover plate mounted on said gas rail with a second inlet orifice and a second outlet orifice formed therethrough;
  wherein said first inlet orifice and said second inlet orifice are aligned to form an inlet port and said first outlet orifice and said second outlet orifice are aligned to form an outlet port;
  wherein said slider plate is slidingly engaged between said guide plate and said cover plate so as to simultaneously open or simultaneously close said inlet passage and said outlet passage.

7. The monitoring chamber of claim 6 further comprising a heating source affixed to said gas rail housing adapted to heat the gas contained between the said monitoring chamber and said gas rail.

8. The monitoring chamber of claim 1 further comprising a gas inlet port into said balancing chamber.

9. The monitoring chamber of claim 1 further comprising:
  a first high temperature seal connecting said quartz tube to said outlet end of said sensor chamber; and
  a second high temperature seal connecting said quartz tube to said proximal end of said balancing chamber.

10. The monitoring chamber of claim 6 further comprising a reversible electric motor coupled to a screw drive that is connected to said blast gate to open or block said inlet passage and said outlet passage.

* * * * *